United States Patent [19]

Conrow et al.

[11] Patent Number: 4,591,604
[45] Date of Patent: May 27, 1986

[54] METHOD OF INHIBITING THE COMPLEMENT SYSTEM BY ADMINISTERING MULTISULFONATED NAPHTHALENE UREAS

[75] Inventors: Ransom B. Conrow, Pearl River; Seymour Bernstein, New City, both of N.Y.

[73] Assignee: American Cyanamid Company, Stamford, Conn.

[21] Appl. No.: 644,609

[22] Filed: Aug. 27, 1984

Related U.S. Application Data

[60] Division of Ser. No. 594,447, Mar. 28, 1984, which is a continuation-in-part of Ser. No. 413,938, Sep. 1, 1982, abandoned, which is a continuation-in-part of Ser. No. 334,941, Dec. 28, 1981, abandoned.

[51] Int. Cl.$^4$ .......................................... A61K 31/185
[52] U.S. Cl. ................................................... 514/577
[58] Field of Search .......................... 260/506, 456 A; 424/315; 514/577

[56] References Cited

U.S. PATENT DOCUMENTS

| | | | |
|---|---|---|---|
| 656,646 | 8/1900 | Israel et al. | 260/506 |
| 677,514 | 7/1901 | Israel et al. | 260/506 |
| 677,515 | 7/1901 | Israel et al. | 260/506 |
| 677,516 | 7/1901 | Israel et al. | 260/506 |
| 3,679,420 | 7/1972 | Yokoyama et al. | 260/506 |

*Primary Examiner*—Nicky Chan
*Attorney, Agent, or Firm*—Susan H. Rauch; Anne M. Rosenblum

[57] ABSTRACT

A method of inhibiting the complement system using multisulfonated naphthalene ureas.

15 Claims, No Drawings

METHOD OF INHIBITING THE COMPLEMENT SYSTEM BY ADMINISTERING MULTISULFONATED NAPHTHALENE UREAS

This is a division of our co-pending application, Ser. No. 594,447, filed Mar. 28, 1984, which in turn is a continuation-in-part of Ser. No. 413,938, filed Sept. 1, 1982, now abandoned, which is a continuation-in-part of Ser. No. 334,941, filed Dec. 28, 1981, abandoned.

BACKGROUND OF THE INVENTION

1. Field of the Invention

The present invention relates to novel multisulfonated naphthalene ureas and their use as inhibitors of the complement system of warm-blooded animals.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973): Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 850 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anti-complementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973);

J. Immunol. 113: 584 (1974); Immunology 26: 819 (1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23:240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

It has now been discovered that multisulfonated naphthalene ureas interact with the complement reaction sequence, thereby inhibiting complement activity in body fluids.

This invention also concerns a method of inhibiting the complement system in a body fluid which comprises subjecting body fluid complement to the action of an effective complement inhibiting amount of the above-identified compounds. This invention further deals with a method of inhibiting the complement system in a warm-blooded animal which comprises administering to said animal an effective complement inhibiting amount of the above described compounds.

DETAILED DESCRIPTION OF THE INVENTION

In accordance with the present invention, there are provided novel compounds represented by the following generic Formula I:

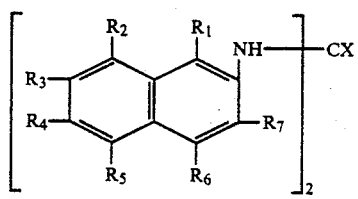

FORMULA I wherein $R_1$ is hydrogen or $-SO_3A$; $R_2$ is hydrogen, hydroxy, $-SO_3A$ or phenylsulfonyloxy; $R_3$ is hydrogen or $-SO_3A$; $R_4$ is hydrogen, nitro, amino or $-SO_3A$; $R_5$ is hydrogen or $-SO_3A$; $R_6$ is hydrogen or $-SO_3A$; $R_7$ is hydrogen or $-SO_3A$; X is oxygen or sulfur; and A is a nontoxic pharmaceutically acceptable salt; provided that the naphthyl ring must contain at least one sulfonic acid group or no more than three sulfonic acid groups at the same time; and further provided that if $R_2$ is hydroxy and $R_4$ is $-SO_3A$ when X is oxygen, then at least one member selected from $R_1$, $R_3$, $R_5$, $R_6$ or $R_7$ must be $-SO_3A$.

Particularly preferred compounds of Formula I which are of major interest as complement inhibitors include the following:

3,3'-Ureylenedi-2,7-naphthalenedisulfonic acid, tetrasodium salt 3,3'-Ureylenebis(7-nitro-1,5-naphthalenedisulfonic acid), tetrasodium salt 7,7'-Ureylenedi-1,3,5-naphthalenetrisulfonic acid, hexasodium salt.

3,3'-Ureylenebis(5-hydroxy-2,7-naphthalenedisulfonic acid), tetrasodium salt.

The instant invention also includes novel compounds represented by the following generic Formula II:

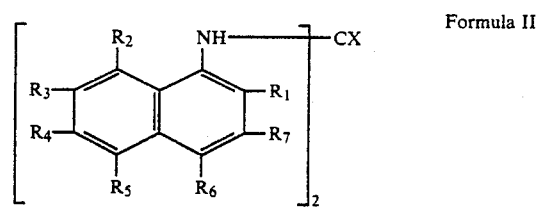

Formula II wherein $R_1$ is hydrogen or $-SO_3A$; $R_2$ is hydrogen, hydroxy, $-SO_3A$ or phenylsulfonyloxy; $R_3$ is hydrogen or $-SO_3A$; $R_4$ is hydrogen, nitro, amino or $-SO_3A$; $R_5$ is hydrogen or $-SO_3A$; $R_6$ is hydrogen or $-SO_3A$; $R_7$ is hydrogen or $-SO_3A$; X is oxygen or sulfur; and A is a nontoxic pharmaceutically acceptable salt; provided that the naphthyl ring must contain at least one sulfonic acid group or no more than three sulfonic acid groups at the same time; and further provided that if $R_2$ is hydroxy and $R_4$ is $-SO_3A$ when X is oxygen, then at least one member selected from $R_1$, $R_3$, $R_5$, $R_6$ or $R_7$ must be $-SO_3A$.

Particularly preferred compounds of Formula II which are of major interest as complement inhibitors include the following:

8,8'-Ureylenedi-1,3,6-naphthalenetrisulfonic acid, hexasodium salt 8,8'-(2-Thioureylene)di-1,3,6-naphthalenetrisulfonic acid, hexasodium salt 8,8'-Ureylenedi-1,3,5-naphthalenetrisulfonic acid, hexasodium salt 4,4'-Ureylenedi-1-naphthalenesulfonic acid, disodium salt 4,4'-Ureylenedi-2,7-naphthalenedisulfonic acid, tetrasodium salt 4,4'-Ureylenedi-2,6-naphthalenedisulfonic acid, tetrasodium salt 4,4'-Ureylenedi-1,6-naphthalenedisulfonic acid, tetrasodium salt 4,4'-Ureylenebis(5-hydroxy-2,7-naphthalenedisulfonic acid), tetrasodium salt dibenzenesulfonate 8,8'-Ureylenedi-1,6-naphthalenedisulfonic acid, tetrasodium salt The present invention further concerns novel compounds represented by the following generic Formula III:

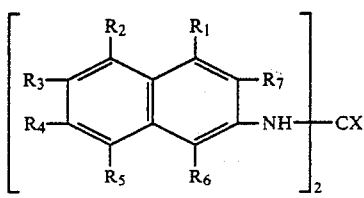

Formula III wherein $R_1$ is hydrogen or $-SO_3A$; $R_2$ is hydrogen, $-SO_3A$ or phenylsulfonyloxy; $R_3$ is hydrogen or $-SO_3A$; $R_4$ is hydrogen, nitro, amino or $-SO_3A$; $R_5$ is hydrogen or $-SO_3A$; $R_6$ is hydrogen or $-SO_3A$; $R_7$ is hydrogen or $-SO_3A$; X is oxygen or sulfur; and A is a nontoxic pharmaceutically acceptable salt; provided that the naphthyl ring must contain at least one sulfonic acid group or no more than three sulfonic acid groups at the same time.

A particularly preferred compound of Formula III which is of major interest as a complement inhibitor includes the following:

6,6'-Ureylenedi-1,3-naphthalenedisulfonic acid, tetrasodium salt

This invention is also concerned with known compounds prepared by Brass and co-workers as recited in Elsevier's Encyclopedia of Org. Chem., vol. 12B at p. 5375 and p. 5386 (1955) and illustrated as Formulas IV and V:

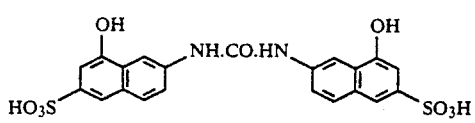

Formula IV

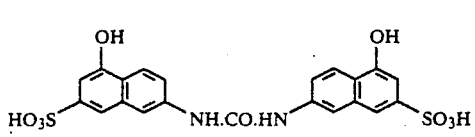

Formula V

Specific known compounds of Formulas IV and V, respectively, which are of particular interest showing novel activity as complement inhibitors are 7,7'-ureylenebis(1-hydroxy-3-naphthalenesulfonic acid), 6,6'-ureylenebis(1-hydroxy-3-naphthalenesulfonic acid) and the disodium salts thereof.

This invention further deals with a method of inhibiting the complement system in a body fluid, such as blood serum, which comprises subjecting body fluid complement to the action of an effective complement inhibiting amount of a compound of the above formulas. Body fluids can include blood, plasma, serum, synovial fluid, cerebrospinal fluid, or pathological accumulations of fluid such as pleural effusion, etc. This invention also concerns a method of inhibiting the complement system in a warm-blooded animal which comprises administering to said warm-blooded animal an effective complement inhibiting amount of a compound of the above formulas.

The above compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occlusion. They may also be useful in the treatment of transplant rejection and ulcers and as blood culture and transport mediums.

The compounds of the present invention may be prepared according to the following flowcharts:

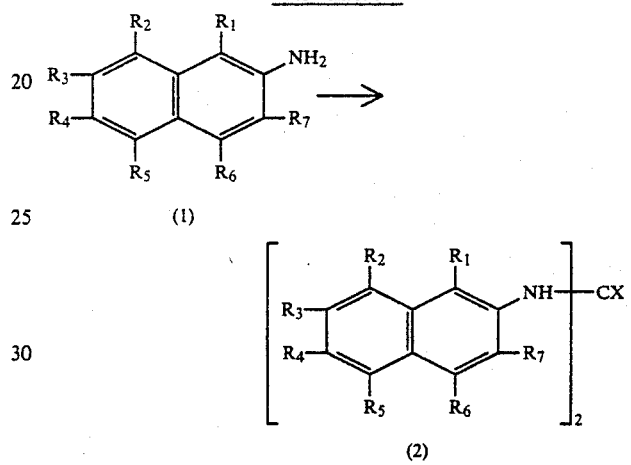

wherein $R_1$, $R_2$, $R_3$, $R_4$, $R_5$, $R_6$ and $R_7$ are as above defined.

General Procedure A

Phosgene is bubbled into a vigorously stirred and cooled aqueous solution of the amino acid (1) and sodium carbonate (at a ratio of 2–5 moles of sodium carbonate per mole of amine) until the solution is acidic. The reaction is monitored by thin-layer electrophoresis or thin-layer chromatography. If required, more sodium carbonate is added and phosgenation is repeated until the mixture is acidic. The mixture is made weakly basic with sodium hydroxide or sodium carbonate, and ethanol is added to precipitate the product (2). The solid is collected by filtration, washed successively with aqueous ethanol, ethanol and ether and dried by conventional procedures.

General Procedure B

An aqueous solution of the amino acid (1) and pyridine (at a ratio of 5-9 moles of pyridine per mole of amine) is phosgenated as described in General Procedure A and then made strongly basic with sodium hydroxide. The product is recovered as described in General Procedure A.

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g. toxicity, effectiveness, etc) of the parent compound. The salt forming moieties of the present invention which are pharmaceutically acceptable include the alkali metals (e.g., sodium, potassium, etc.) alkaline earth metals (e.g., calcium, etc.); ammonia; and substituted ammonia selected from the group consisting of trialkylamine ($C_1$–$C_6$), piperidine, pyrazine, alkanolamine ($C_2$–$C_6$) and cycloalkylamine ($C_3$–$C_6$).

The term "trialkylamine ($C_1$–$C_6$)" defines those amines having three aliphatic fully saturated hydrocarbon substituents containing 1 to 6 carbon atoms either linearly or branched. Typically, these amines are trimethylamine, triethylamine, tripropylamine, dimethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

2,2'-Ureylenedi-1,5-naphthalenedisulfonic acid, tetrasodium salt

A solution of 12.12 g of 2-naphthylamine-1,5-disulfonic acid in 75 ml of water and 20 ml of pyridine was treated with gaseous phosgene until acidic. The solution was neutralized with pyridine, diluted with 500 ml of ethanol and made basic with 12.8 g of sodium hydroxide. The mixture was stirred, then the precipitate was collected, dissolved in 100 ml of 1N sodium hydroxide, evaporated in vacuo and cooled. The solid was collected, washed with water and dried at 110° C., giving 8.02 g of the desired product.

EXAMPLE 2

1,1'-Ureylenedi-2-naphthalenesulfonic acid

A solution of 8.93 g of 1-amino-2-naphthalenesulfonic acid in 100 ml of water and 16 ml of pyridine was phosgenated as described in Example 1, giving 2.5 g of the desired product.

EXAMPLE 3

4,4'-Ureylenebis(5-hydroxy-2,7-naphthalenedisulfonic acid), tetrasodium salt dibenzenesulfonate A solution of 4.95 g of 4-amino-5-hydroxybenzenesulfonate-2,7-naphthalenedisulfonic acid in 40 ml of water and 7.5 ml of pyridine was phosgenated as described in Example 1, giving 200 mg of the desired product.

EXAMPLE 4

8,8'-Ureylenedi-1,3,6-naphthalenetrisulfonic acid, hexasodium salt

A solution of 51.2 g of 8-amino-1,3,6-naphthalenetrisulfonic acid disodium salt in 120 ml of water containing 21.0 ml of 5N sodium hydroxide was warmed and filtered. The filtrate was slowly diluted with 400 ml of ethanol, stirred and allowed to cool to room temperature. The solid was collected, washed with ethanol, then ether and dried, giving 46.0 g of 8-amino-1,3,6-naphthalenetrisulfonic acid, trisodium salt.

A solution of 2.0 g of 8-amino-1,3,6-naphthalenetrisulfonic acid, trisodium salt and 0.93 g of sodium carbonate in 15 ml of water was phosgenated until acidic, neutralized with 150 mg of sodium carbonate, heated on a steam bath and diluted with 30 ml of ethanol. The solid was collected, washed with aqueous ethanol (1:2), ethanol, then ether and dried, giving 1.5 g of the desired product.

EXAMPLE 5

3,3'-Ureylenedi-2,7-naphthalenedisulfonic acid, tetrasodium salt

A solution of 13.01 g of 3-amino-2,7-naphthalenedisulfonic acid, monosodium salt and 21 g of sodium carbonate in 75 ml of water was phosgenated as described in Example 4, giving 3.61 g of the desired product.

EXAMPLE 6

5,5'-Ureylenedi-1-naphthalenesulfonic acid, disodium salt

A solution of 8.93 g of 5-amino-1-naphthalenesulfonic acid and 21 g of sodium carbonate in 100 ml of water was phosgenated as described in Example 4, giving 1.83 g of the desired product.

EXAMPLE 7

8,8'-(2-Thioureylene)di-1,3,6-naphthalenetrisulfonic acid, hexasodium salt

To a solution of 32.0 g of 8-amino-1,3,6-naphthalenetrisulfonic acid, trisodium salt in 350 ml of water and 7.0 ml of concentrated hydrochloric acid was added 10.0 g of thiophosgene. The mixture was stirred 2½ hours, treated with charcoal and filtered through diatomaceous earth. The filtrate was neutralized with 46 ml of 5N sodium hydroxide, chilled and the solid was collected and recrystallized from 40 ml of water by heating and then chilling in an ice bath. This solid was washed with ice water, acetone then ether and dried, giving 11.2 g of 8-isothiocyanato-1,3,6-naphthalenetrisulfonic acid, trisodium salt.

A solution of 5.0 g of 8-isothiocyanato-1,3,6-naphthalenetrisulfonic acid, trisodium salt in 20 ml of water was heated on a steam bath for one hour, then cooled and diluted with 40 ml of ethanol. The solid was collected, washed with 66% ethanol, ethanol then ether and dried, giving 4.15 g of the desired product.

EXAMPLE 8

4,4'-Ureylenedi-2,6-naphthalenedisulfonic acid, tetrasodium salt

A suspension of 15.15 g of 1-amino-3,7-naphthalenedisulfonic acid, 20 ml of 5N sodium hydroxide and 14.6 g of sodium carbonate in 150 ml of water was phosgenated as described in Example 4, giving 7.0 g of the desired product.

EXAMPLE 9

4,4'-Ureylenedi-1,6-naphthalenedisulfonic acid, tetrasodium salt

A solution 15.15 g of 1-amino-4,7-naphthalenedisulfonic acid, 20.0 ml of 5N sodium hydroxide and 10.6 g of sodium carbonate in 100 ml of water was phosgenated as described in Example 4, giving 6.8 g of the desired product.

EXAMPLE 10

8,8'-Ureylenedi-1,6-naphthalenedisulfonic acid, tetrasodium salt

A solution of 15.15 g of 1-amino-3,8-naphthalenedisulfonic acid, 14.6 g of sodium carbonate, 20.0 ml of 5N sodium hydroxide and 50 ml of water was phosgenated as described in Example 4, giving 13.8 g of the desired product.

EXAMPLE 11

3,3'-Ureylenebis(7-nitro-1,5-naphthalenedisulfonic acid), tetrasodium salt

A 100 g portion of 3-amino-7-nitro-1,5-naphthalenedisulfonic acid was slurried in 800 ml of water, the pH was adjusted to 8–9, the mixture was concentrated until a solid began to precipitate and then allowed to stand overnight. The solid was collected, washed with cold water, ethanol then ether and dried, giving 34 g of 3-amino-7-nitro-1,5-naphthalenedisulfonic acid, disodium salt.

A 7.84 g portion of the above product and 8.4 g of sodium carbonate in water was phosgenated as described in Example 4, giving 5 g of the desired product.

EXAMPLE 12

7,7'-Ureylenedi-1,3,5-naphthalenetrisulfonic acid, hexasodium salt

A 450 g portion of 2-amino-6-nitro-4,8-naphthalenedisulfonic acid was dissolved in 2.3 liters of water and basified to pH 9 with 5N sodium hydroxide. After standing 48 hours, the solid was collected, washed with ethanol and dried, giving 193 g of 2-amino-6-nitro-4,8-naphthalenedisulfonic acid, disodium salt.

To a heavy paste of 78.0 g of the above disodium salt in water was added 15.0 g of sodium nitrite. This mixture was then slowly added to a cooled solution of 80.0 ml of concentrated hydrochloric acid in 40 ml of water, maintaining the temperature at 0°–5° C. A solution of 4.6 g of cupric chloride in 4 ml of water was added to a solution of 200 ml of glacial acetic acid saturated with sulfur dioxide. This mixture was added to the above diazonium salt mixture slowly, maintaining the temperature at 5°–7° C. Additional water was introduced to aid stirring. The mixture was stirred for 2 hours then stored in a chill room for 48 hours. The solvent was removed, the residue was dissolved in water, basified to pH 9–10 with sodium carbonate and filtered. The filtrate was concentrated, then diluted with ethanol and the solid was collected, washed with ethanol and ether and dried, giving 70.0 g of 3-nitro-1,5,7-naphthalenetrisulfonic acid, trisodium salt. A 26 g portion of this trisodium salt was catalytically reduced giving 12 g of 3-amino-1,5,7-naphthalenetrisulfonic acid, trisodium salt. A 5.0 g portion of this amino derivative and 2.5 g of sodium bicarbonate in water was phosgenated as described in Example 4, giving 4.3 g of the desired product.

EXAMPLE 13

6,6'-Ureylenedi-1,3-naphthalenedisulfonic acid, tetrasodium salt

A mixture of 6.06 g of 6-amino-1,3-naphthalenedisulfonic acid and 10.5 g of sodium carbonate in 50 ml of water was phosgenated as described in Example 4, giving 7.2 g of the desired product.

EXAMPLE 14

4,4'-Ureylenedi-1-naphthalenesulfonic acid, disodium salt

A mixture of 10.17 g of 4-amino-1-naphthalenesulfonic acid and 8.40 g of sodium carbonate in 100 ml of water was phosgenated as described in Example 4, giving 7.81 g of the desired product.

EXAMPLE 15

4,4'-Ureylenedi-2,7-naphthalenedisulfonic acid, tetrasodium salt

A mixture of 12.12 g of 4-amino-2,7-naphthalenedisulfonic acid and 21 g of sodium bicarbonate in 75 ml of water was phosgenated as described in Example 4, giving 14.41 g of the desired product.

EXAMPLE 16

8,8'-Ureylenedi-1,3,5-naphthalenetrisulfonic acid, hexasodium salt

To a warm solution of 23.8 g of 8-amino-1,3,5-naphthalenetrisulfonic acid in 25 ml of water and 25 ml of 5N sodium hydroxide was slowly added with vigorous stirring 125 ml of ethanol. The mixture was cooled to room temperature and the solid was collected, washed with 80% ethanol, ethanol then ether and dried, giving 21.0 g of 8-amino-1,3,5-naphthalenetrisulfonic acid, trisodium salt.

A 4.35 g portion of the above trisodium salt and sodium carbonate in 15 ml of water was phosgenated as described in Example 4, giving 1.85 g of the desired product.

EXAMPLE 17

3,3'-Ureylenebis(5-hydroxy-2,7-naphthalenedisulfonic acid), tetrasodium salt

A mixture of 7.25 g of 3-amino-5-hydroxy-2,7-naphthalenedisulfonic acid, disodium salt and 5.1 g of sodium bicarbonate in 75 ml of water was phosgenated as described in Example 4, giving 1.6 g of the desired product.

EXAMPLE 18

Preparation of Compressed Tablet

| Ingredient | mg/Tablet |
|---|---|
| Active Compound | 0.5–500 |
| Dibasic Calcium Phosphate NF | qs |
| Starch USP | 40 |
| Modified Starch | 10 |
| Magnesium Stearate USP | 1–5 |

EXAMPLE 19

Preparation of Compressed Tablet-Sustained Action

| Ingredient | mg/Tablet |
|---|---|
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 20

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 21

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 22

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 23

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 24

Preparation of Injectable Solution

| Ingredient | % W/V |
|---|---|
| Active Compound | 0.05–5 |
| Benzyl Alcohol NF | 0.9 |
| Water for Injection | 100.0 |

EXAMPLE 25

Preparation of Injectable Oil

| Ingredient | % W/V |
|---|---|
| Active Compound | 0.05–5 |
| Benzyl Alcohol | 1.5 |
| Sesame Oil qs ad | 100.0 |

EXAMPLE 26

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1.5% |
| pH adjusted to 5.0–7.5 | |
| Water for Injection qs ad | 100% |

EXAMPLE 27

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6–8 | qs |
| Water for Injection qs ad | 100.0 |

EXAMPLE 28

Preparation of Dental Paste

| Ingredient | % W/W |
|---|---|
| Active Compound | 0.05–5 |
| Zinc Oxide | 15 |
| Polyethylene Glycol 4000 USP | 50 |
| Distilled Water qs | 100 |

EXAMPLE 29

Preparation of Dental Ointment

| Ingredient | % W/W |
|---|---|
| Active Compound | 0.05–5 |
| Petrolatum, White USP qs | 100 |

EXAMPLE 30

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 31

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Distilled Water qs | 100 |

EXAMPLE 32

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 33

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 34

Preparation of Buccal Tablet

| Ingredient | mg/Tablet |
|---|---|
| Active Ingredient | 3.25 |
| 6x Sugar | 290.60 |
| Acacia | 14.53 |
| Soluble Starch | 14.53 |
| F. D. & C. Yellow No. 6 Dye | 0.49 |
| Magnesium Stearate | 1.60 |
| | 325.00 |

The final tablet will weigh about 325 mg and may be compressed into buccal tablets in flat faced or any other tooling shape convenient for buccal administration.

EXAMPLE 35

Preparation of Lozenge

| Ingredient | g/Lozenge |
|---|---|
| Active Ingredient | 0.0140 |
| Kompact ® Sugar (Sucrest Co.) | 0.7138 |
| 6x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about .5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iii) Cap 50 Test—Here, appropriate amounts of the test compound are added to a pool of guinea pig serum in vitro, after which the complement level is determined in undiluted serum by the serum capillary tube assay of U.S. Pat. No. 3,876,376. The concentration of compound inhibiting 50% is reported; and (iv) Guinea Pig Intraperitoneal Test (GPIP)—Guinea pigs weighing about 300 g are dosed intraperitoneally (i.p.) with 200 mg/kg of the test compound dissolved in saline and adjusted to pH 7-8. Approximately 0.4 ml blood samples, taken by orbital sinus puncture 30 minutes and one hour after injections, are collected directly into centrifuge tubes; 5 ml blood samples, taken by decapitation 2 hours after injection, are collected directly into diSPo ® beakers. The samples were allowed to clot, centrifuged, and the resultant sera were assayed for complement activity using the capillary complement assay. Percent inhibition is calculated by comparison with simultaneous controls. The results of the GPIP appear in Table I together with results of Test Code 026, 036 and Cap 50. Table I shows that the principal compounds of the invention possess highly significant complement inhibiting activity in warm-blooded animals.

TABLE I

Biological Activities

| Compound | In vitro Activity Cl 026* Wells | C-Shunt Inhibition 036* Wells | Cap 50 | In vivo Activity Guinea Pigs Intraperitoneal % Lowering Time (minutes) 30 | 60 | 120 |
|---|---|---|---|---|---|---|
| 7,7'-Ureylenebis(1-hydroxy-3-naphthalenesulfonic acid) | +2** | | | | | |
| 6,6'-Ureylenebis(1-hydroxy-3-naphthalenesulfonic acid), disodium salt | +1 | | | | | |
| 8,8'-Ureylenedi-1,3,6-naphthalenetrisulfonic acid, hexasodium salt | +5 | | 180 | 25 | 61 | 65 |
| 6,6'-Ureylenedi-1,3-naphthalenedisulfonic acid, tetrasodium salt | +3 | | | | | |
| 4,4'-Ureylenedi-1-naphthalenesulfonic acid, disodium salt | +2 | | | | | |
| 3,3'-Ureylenedi-2,7-naphthalenedisulfonic acid, tetrasodium salt | +3 | | | | | |
| 8,8'-(2-Thioureylene)di-1,3,6-naphthalenetrisulfonic acid, hexasodium salt | +5 | | 155 | 41 | 20 | 42 |
| 4,4'-Ureylenedi-2,7-naphthalenedisulfonic acid, tetrasodium salt | +3 | | >500 | | | |
| 8,8'-Ureylenedi-1,3,5-naphthalenetrisulfonic acid, hexasodium salt | | | 12 | 92 | 92 | 94 |
| 4,4'-Ureylenedi-1,6-naphthalenedisulfonic acid, tetrasodium salt | +3 | | >500 | | | |
| 4,4'-Ureylenedi-2,6-naphthalenedisulfonic acid, tetrasodium salt | +2 | | | | | |
| 4,4'-Ureylenebis(5-hydroxy-2,7-naphthalenedisulfonic acid), tetrasodium salt dibenzenesulfonate | +3 | | >500 | | | |
| 8,8'-Ureylenedi-1,6-naphthalenedisulfonic acid, tetrasodium salt | +3 | | >500 | | | |
| 3,3'-Ureylenebis(7-nitro-1,5-naphthalenedisulfonic acid), tetrasodium salt | +3 | | >500 | | | |
| 7,7'-Ureylenedi-1,3,5-naphthalenetrisulfonic acid, hexasodium salt | +6 | +1 | 280 | | | |
| 3,3'-Ureylenebis(5-hydroxy-2,7-naphthalenedisulfonic acid), tetrasodium salt | +4 | | 90 | 4 | 1 | 28 |

*Tests identified by code herein.
**Activity in wells, a serial dilution assay; higher well number indicates higher activity. The serial dilutions are two-fold.

We claim:

1. A method of inhibiting the complement system in a warm-blooded animal which comprises administering orally, topically, periodontally in the oral cavity, intraarticularly or parenterally to said warm-blooded animal an effective complement-imhibiting amount of the compound 3,3'-ureylenedi-2,7-naphthalenedisulfonic acid, tetrasodium salt.

2. A method of inhibiting the complement system in a warm-blooded animal which comprises administering orally, topically, periodontally in the oral cavity, intraarticularly or parenterally to said warm-blooded animal an effective complement-inhibiting amount of the compound 3,3'-ureylenebis(7-nitro-1,5-naphthalenedisulfonic acid), tetrasodium salt.

3. A method of inhibiting the complement system in a warm-blooded animal which comprises administering orally, topically, periodontally in the oral cavity, intraarticularly or parenterally to said warm-blooded animal an effective complement-inhibiting amount of the compound 7,7'-ureylenedi-1,3,5-naphthalenetrisulfonic acid, hexasodium salt.

4. A method of inhibiting the complement system in a warm-blooded animal which comprises administering orally, topically, periodontally in the oral cavity, intraarticularly or parenterally to said warm-blooded animal an effective complement-inhibiting amount of the compound 3,3'-ureylenebis(5-hydroxy-2,7-naphthalenedisulfonic acid), tetrasodium salt.

5. A method of inhibiting the complement system in a warm-blooded animal which comprises administering orally, topically, periodontally in the oral cavity, intraarticularly or parenterally to said warm-blooded animal an effective complement-inhibiting amount of the compound 8,8'-ureylenedi-1,3,6-naphthalenetrisulfonic acid, hexasodium salt.

6. A method of inhibiting the complement system in a warm-blooded animal which comprises administering orally, topically, periodontally in the oral cavity, intraarticularly or parenterally to said warm-blooded animal an effective complement-inhibiting amount of the compound 8,8'-(2-thioureylene)di-1,3,6-naphthalenetrisulfonic acid, hexasodium salt.

7. A method of inhibiting the complement system in a warm-blooded animal which comprises administering orally, topically, periodontally in the oral cavity, intraarticularly or parenterally to said warm-blooded animal an effective complement-inhibiting amount of the compound 4,4'-ureylenedi-2,6-naphthalenedisulfonic acid, tetrasodium salt.

8. A method of inhibiting the complement system in a warm-blooded animal which comprises administering orally, topically, periodontally in the oral cavity, intraarticularly or parenterally to said warm-blooded animal an effective complement-inhibiting amount of the compound 4,4'-ureylenedi-1,6-naphthalenedisulfonic acid, tetrasodium salt.

9. A method of inhibiting the complement system in a warm-blooded animal which comprises administering orally, topically, periodontally in the oral cavity, intraarticularly or parenterally to said warm-blooded animal an effective complement-inhibiting amount of the compound 8,8'-ureylenedi-1,6-naphthalenedisulfonic acid, tetrasodium salt.

10. A method of inhibiting the complement system in a warm-blooded animal which comprises administering orally, topically, periodontally in the oral cavity, intraarticularly or parenterally to said warm-blooded animal an effective complement-inhibiting amount of the compound 8,8'-ureylenedi-1,3,5-naphthalenetrisulfonic acid, hexasodium salt.

11. A method of inhibiting the complement system in a warm-blooded animal which comprises administering orally, topically, periodontally in the oral cavity, intraarticularly or parenterally to said warm-blooded animal an effective complement-inhibiting amount of the compound 4,4'-ureylenedi-1-naphthalenesulfonic acid, disodium salt.

12. A method of inhibiting the complement system in a warm-blooded animal which comprises administering orally, topically, periodontally in the oral cavity, intraarticularly or parenterally to said warm-blooded animal an effective complement-inhibiting amount of the compound 4,4'-ureylenedi-2,7-naphthalenedisulfonic acid, tetrasodium salt.

13. A method of inhibiting the complement system in a warm-blooded animal which comprises administering orally, topically, periodontally in the oral cavity, intraarticularly or parenterally to said warm-blooded animal an effective complement-inhibiting amount of the compound 6,6'-ureylenedi-1,3-naphthalenedisulfonic acid, tetrasodium salt.

14. A method of inhibiting the complement system in a warm-blooded animal which comprises administering orally, topically, periodontally in the oral cavity, intraarticularly or parenterally to said warm-blooded animal an effective complement inhibiting amount of the compound 7,7'-ureylenebis(1-hydroxy-3-naphthalenesulfonic acid).

15. A method of inhibiting the complement system in a warm-blooded animal which comprises administering orally, topically, periodontally in the oral cavity, intraarticularly to parenterally to said warm-blooded animal an effective complement inhibiting amount of the compound 6,6'-ureylenebis(1-hydroxy-3-naphthalenesulfonic acid), disodium salt.

* * * * *